United States Patent
Hilarius et al.

(12)

(10) Patent No.: US 6,534,682 B1
(45) Date of Patent: Mar. 18, 2003

(54) N(CF$_3$)$_2$ ANION GENERATION AND ITS USE

(75) Inventors: Völker Hilarius, Gross-Umstadt (DE); Herwig Buchholz, Frankfurt (DE); Peter Sartori, Rheinberg (DE); Nikolai Ignatiev, Duisburg (DE); Andrei Kucherina, Kiew (UA); Sergii Datsenko, Kiew (UA)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/890,467

(22) PCT Filed: Jan. 19, 2000

(86) PCT No.: PCT/EP00/00372

§ 371 (c)(1),
(2), (4) Date: Aug. 1, 2001

(87) PCT Pub. No.: WO00/46180

PCT Pub. Date: Aug. 10, 2000

(30) Foreign Application Priority Data

Feb. 1, 1999 (EP) .............................................. 99101982

(51) Int. Cl.$^7$ ............................................. C07C 209/62
(52) U.S. Cl. ....................... 564/404; 564/468; 556/110; 556/118; 423/383
(58) Field of Search .......................... 423/383; 556/110, 556/118; 564/404, 468

(56) References Cited

PUBLICATIONS

Database CAPLUS on STN, Acc. No. 1975:409063, Gontar et al., 'Bis(trifluoromethyl)amide (anion).' Zh. Vses. Khim. O–va (1975), 20(2), pp. 232–233 (abstract).*

Young, J.A. et al.: "Fluorocarbon Nitrogen compounds. IV. The Reaction of Metallic Fluorides with Carbon–Nitrogen Unsaturation in Perfluoro–2–azapropene" Journal of the American Chemical Society, vol. 81, 1959, pp. 1587–1589, XP000882386.

Young, J.A. et al.: "Fluorocarbon Nitrogen Compounds. VIII. Mono–, Di–, Tri– and Tetra–acyl Derivatives, Oxadiazoles and omega–Bromo Acyl Isocyanates" Journal of the American Chemical Society, vol. 84, 1962, pp. 2105–2109, XP000882388.

Gontar', A.F. et al.: "Generation and Some Reactions of Bis(trifluoromethyl)aza Anion" Bulletin of the Academy of Science of the USSR, Division Chemical Science (English Translation), vol. 24, No. 10, 1975, pp. 2161–2164, XP000882539.

* cited by examiner

*Primary Examiner*—Brian Davis
(74) *Attorney, Agent, or Firm*—Millen, White, Zelano & Branigan, P.C.

(57) ABSTRACT

The invention relates to a process of generating N(CF$_3$)$_2$ anions by reacting a metal fluoride of formula MF$_x$ with a compound of formula R$_F$SO$_2$N(CF$_3$)$_2$, (CF$_3$)$_2$N(SO$_2$CF$_2$)$_m$SO$_2$N(CF$_3$)$_2$ or R$_F$CON(CF$_3$)$_2$. The invention further relates to the use of the N(CF$_3$)$_2$ anions as a reagent for the introduction of halogen or other organic groups into organic molecules.

18 Claims, No Drawings

N(CF$_3$)$_2$ ANION GENERATION AND ITS USE

This invention relates to a new process for the generation of N(CF$_3$)$_2$ anions and their use for the introduction of N(CF$_3$)$_2$-groups into organic molecules.

The chemistry of bis(trifluoromethyl)imido-anion is generally based on the chemical transformation of perfluoro(2-azapropene), CF$_3$N=CF$_2$, as a starting material (H. G. Ang and Y. C. Syn, Advances in Inorganic Chemistry and Radiochemistry, Vol. 16 (1974), p. 1–64; A. Haas, Gmelin Handbook of Inorganic Chemistry, 8th edition, Springer Verlag: Berlin Heidelberg New York (1981), Part 9, p. 125–153; A. Haas, Gmelin Handbook of Inorganic Chemistry, 8th edition, Springer-Verlag: Berlin - Heidelberg New York (1991), Suppl. Vol. 6, p. 196–214). This compound can be prepared in 78% yield by fluorination of CCl$_3$N=CCl$_2$ with excess of NaF in sulfolane at 105° C. (E. Klauke, H. Holtschmidt, K. Findeisen, Farbenfabriken Bayer A.-G., DE-A1-21 01 107 (1971/72) or by photolysis of CF$_3$N—(CF$_2$CFCl$_2$)Cl (Yield: 65–70%) (G. Sarwar, R. L. Kirchmeier and J. M. Shreeve, Inorg. Chem. 28 (1989, p. 2187–2189). Perfluoro(2-azapropene) is a gas at room temperature (B.p. −33° C.) and to make use of this compound a special equipment is required.

Very reactive di[bis(trifluoromethyl)imido]mercury, Hg[N(CF$_3$)$_2$]$_2$, was synthesised at first by Young and co-workers (J. A. Young, S. N. Tsoukalas and R. D. Dresdner, J. Am. Chem. Soc. 80 (1958), p. 3604–3606). This compound is a good reagent for the introduction of N(CF$_3$)$_2$-groups into organic molecules (H. G. Ang and Y. C. Syn, Advances in Inorg. Chem. and Radiochemistry, Vol. 16 (1974), p. 1–64; A. Haas, Gmelin Handbook of Inorganic Chemistry, 8th edition, Springer Verlag: Berlin Heidelberg New York (1981), Part 9, p. 45–46) but it is a not very stable substance, which is extremely sensitive to the moisture. The synthesis of Hg[N(CF$_3$)$_2$]$_2$ is a hard and time-consuming work which requires special equipment and expensive starting materials.

Caesium bis(trifluoromethyl)imid, Cs$^+$-$^-$N(CF$_3$)$_2$, is another possible candidate for the synthesis of bis(trifluoromethyl)amino compounds. This salt can be prepared simply by bubbling of perfluoro(2-azapropene) into a suspension of caesium fluoride in dry acetonitrile (A. F. Gontar, E. G. Bykovskaja and I. L. Knunyants, Izv. Akad. Nauk SSSR, Otd. Khim, Nauk (1975), p. 2279–2282).

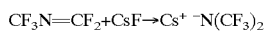

Disadvantage of this method is the formation of a dimeric product by reaction of the starting material perfluoro(2-azapropene) with cesium salt already formed:

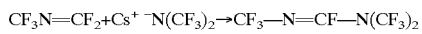

This reaction seems to be nearly unavoidable and leads to the formation of a complex mixture of products.

Accordingly, there is a need for a new process for the generation of N(CF$_3$)$_2$anions and their use for the introduction of N(CF$_3$)-groups into organic molecules. Especially, there is a need for such a new process, which does not need special security equipment, which may be handled in simple manner and avoids the building of undesired by-products at the same time.

The problem is solved by a new process for the generation of N(CF$_3$)$_2$ anions, which is characterised in that a sulphonamide of the general formula

wherein R$_F$ means F or C$_n$F$_{2n+1}$ and n is number between 1 and 4, is reacted with a metal fluoride of the general formula

wherein M is Na, K, Rb, Cs, Ag, Cu or Hg with the proviso that x is 1 or 2, if M means Na, K, Rb, Cs or Ag, and x=2 if M means Cu or Hg, forming an imino salt of the general formula

and the corresponding sulphonylfluoride of the general formula

or
that a sulphondiamide of the formula

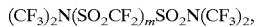

wherein m means 0 or 1, is reacted with a metal fluoride as mentioned above forming an imino salt

and the corresponding sulphonylfluoride

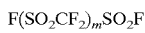

or
that a N,N-Bis(trifluoromethyl)perfluoroacylamide of the general formula

is reacted with said metal fluoride forming said imino salt and a salt of the general formula

The process according to the invention takes place in an organic solvent out of the group acetonitrile, ethylenglycoldimethylether and DMF or mixtures thereof. Preferably it is proceeded in acetonitrile, which is free of water. According to the invention, the reaction may be proceeded at a temperature between 15–100° C. Usually, good results are received at room temperature.

Suitable metal fluorides are fluorides of Na, K, Rb, Cs, Ag, Cu or Hg, but rubidium fluoride is the most preferred.

Advantageously, sulfonylfluorides, which are built as by-products during the reaction, may be collected, transformed again into starting material and may be reused in the inventive process.

The imino salts of the general formula

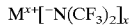

wherein M and x have the meaning given above, may be used as a reagent for the substitution of halogen or other groups in organic molecules. Especially, [bis(trifluoromethyl)imido] rubidium,

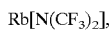

may be used as a reagent for the substitution of halogen or other groups in organic molecules by a N(CF$_3$)$_2$-group.

Recently there has been developed a method for the synthesis of new N,N-bis(trifluoromethyl) perfluoroalkanesulfon-amides and -diamides (N. Ignat'ev, S.

Datsenko, L. Yagupolskii, A. Dimitrov, W. Radek and St. Rudiger, J. Fluorine Chemistry (1995), 74, p. 181–186; P. Sartori, N. Ignat'ev and S. Datsenko, J. Fluorine Chemistry (1995), 75, p. 157–161; P. Sartori, N. Ignat'ev and S. Datsenko, J. Fluorine Chemistry (1995), 75, p. 115–121).

These compounds can be prepared in a one-step procedure based on the use of simple starting materials, for example:

Reaction (I):

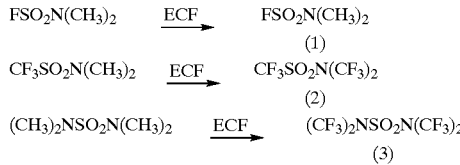

It has been found that sulphonamides (1), (2) and (3) are stable colourless liquids, which are storable for a long time at room temperature (B.p. 30–31° C.; B.p. 56–57° C. and 85–86° C., respectively). The handling of these compounds needs neither special precautions and nor a special equipment is required. Perfluorinated sulphonamides like (1), (2) and (3) are nonhygroscopic substances, even they are not mixable with water, but they are fairly good soluble in organic solvents, such as acetonitrile, ethylenglycoldimethylether, DMF and others, that provide handy conditions for the use of these compounds in organic syntheses.

Now we have found by experiments that perfluorinated sulphonamides (1), (2) and (3) are suitable to react with metal fluorides forming the corresponding sulfonylfluorides and imido salts (4) according to the following general reaction:

Reaction (II):

wherein $R_F$ = F or $C_nF_{2n+1}$ n=1–4

M=Na, K, Rb, Cs, Ag Cu, Hg and x=1 or 2, with the proviso that x=1, if M has the meaning Na, K, Rb, Cs or Ag, and that x=2, if M has the meaning Cu or Hg.

In special, we have found that $(CF_3)_2N(SO_2CF_2)_mSO_2N(CF_3)_2$ may react with a metal fluoride, preferably with an alkali fluoride, according to the following general reaction:

Reaction (IIa):

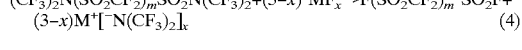

wherein m=0–1.

Rubidium fluoride is the mostly convenient reagent for the complete transformation of sulphonamides type (1)–(3) into imido salt (4).

The reaction may be proceeded at a temperature between 15–100° C., preferably at room temperature, in a suitable organic solvent, which is free of water. The solvent may be chosen out of the group acetonitrile, ethylenglycoldimethylether and DMF, but other polar solvents are also useful.

The most suitable solvent is dry acetonitrile, in which the reaction takes place within a few minutes and results in the formation of rubidium bis(trifluoromethyl)imid. This is a stable salt in solution at room temperature for a long time and may be used for the following synthesis without isolation.

We also have found that N,N-Bis(trifluoromethyl) perfluoroacylamides type (5) are further suitable starting materials for the generation of imido salts (4). These compounds (5) react with metal fluorides according to the following general equation:

Reaction (III):

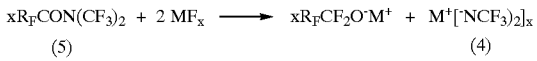

$R_F$ = F or $C_nF_{2n+1}$;

n = 1-4

M = Na, K, Rb, Cs, Ag Cu, Hg and x = 1 or 2, with the proviso that x is 1, if M has the meaning Na, K, Rb, Cs or Ag and that x = 2, if M has the meaning Cu or Hg.

Compounds of type (5) can be prepared by the electrochemical fluorination of corresponding N,N-dimethylperfluoroacylamides as it is described in: J. A. Young, T. C. Simons and F. W. Hoffmann, J. Am. Chem. Soc. (1956), 78, p. 5637–5639.

Perfluorinated sulphonylfluorides that are formed as a by-product according to reaction (II) are either a gas at room temperature or very volatile liquids. At room temperature some amounts of sulfonylfluorides remain in the acetonitrile solution. This does not cause any problem for the introduction of $N(CF_3)_2$ groups into organic and inorganic molecules using imido salts (4).

Sulfonylfluorides resulting from the process (II) preferably are collected from the gaseous phase and may be used again for the following transformation into starting materials for the preparation of sulphonamides of type (1)–(3) by electrochemical fluorination in anhydrous hydrogen fluoride (Simons process). This reaction is for example according to the following equation:

Reaction (IV):

In the combination with the following electrochemical fluorination (Reaction I) this method gives the possibility to transform $N(CH_3)_2$ groups into $N(CF_3)_2$ groups and imido salts (4). Therefore, Reaction IV is based on a cheap and commercially available material: dimethylamine.

In summary, the imido salt (4) is a convenient reagent for the introduction of $N(CF_3)_2$ groups into organic molecules. For example its alkali salts, preferably the rubidium salt, react at mild conditions with benzyl bromide or -chloride and ethyl bromoacetate to form substituted products bearing a $N(CF_3)_2$ group (see reaction (V). In general, these salts seem to be suitable reagents for the substitution of halogen or other groups in organic molecules:

Reaction (V):

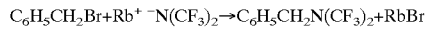

Reaction (VI):

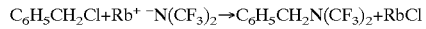

Reaction (VII):

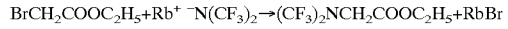

These reactions are given to demonstrate the synthetic utilities of bis(trifluoromethyl)imido salts (4), which can be easily obtained from perfluorinated sulphonamides type (1)–(3) and acylamides type (5) and metal fluorides.

EXAMPLE 1

Preparation of Bis(trifluoromethyl)imido-rubidium and -Potassium Salts from $CF_3SO_2N(CF_3)_2$ To 2.185 g (21 mmol) of RbF in 10 cm$^3$ of dry $CH_3CN$ which are placed in a glass flask equipped with a condenser 6.127 g (21 mmol) of $CF_3SO_2N(CF_3)_2$ were added drop wise. The reaction mixture was stirred at room temperature till all RbF was dissolved (some minutes). The resulting mixture was examined by $^{19}F$ NMR spectroscopy. The signal at −37.5 ppm(s) belongs to the Rb$^+$ $^-N(CF_3)_2$ salt. This was confirmed by addition to the reaction mixture of an identical sample of the Rb$^+$ $^-N(CF_3)_2$ salt, which was prepared by the known procedure [6] from RbF and perfluoro(2-azapropene) in acetonitrile solution.

The similar procedure was used for the preparation of Rb$^+$ $^-N(CF_3)_2$ salt starting with RbF and $FSO_2N(CF_3)_2$.

The acetonitrile solution of Rb$^+$ $^-N(CF_3)_2$ salt, prepared in the way which is described above, is stable at room temperature in a closed flask for a long time and can be used for the following chemical reactions without additional purification (see examples 8, 9).

The bis(trifluoromethyl)imido sodium, potassium and cesium salts can be prepared by the same procedure starting from NaF, KF and CsF, respectively and $CF_3SO_2N(CF_3)_2$ or $FSO_2N(CF_3)_2$, for example:

2.85 g (10 mmol) of $CF_3SO_2N(CF_3)_2$ were added to 0.58 g of KF suspended in 5 cm$^3$ of dry acetonitrile and the reaction mixture was stirred at room temperature for 1 hour. Solution was examined by $^{19}F$ NMR spectroscopy. The signal −39.7 ppm (s) belongs to the K$^+$ $^-N(CF_3)_2$ salt.

Published value for Cs$^+$ $^-N(CF_3)_2$ and K$^+$ $^-N(CF_3)_2$ salts is −34.2 ppm (broad singlet) relatively to $CF_3COOH$ (external standard) (A. F. Gontar, E. G, Bykowskaja and J. L. Knunyants, Izv. Akad. Nauk SSR, Otd. Khim. Nauk (1975), p. 2279–2282).

EXAMPLE 2

Preparation of Bis(trifluoromethyl)imido-rubidium Salt from $C_4F_9SO_2N(CF_3)_2$ To 0.041 g (0.39 mmol) of RbF in 1 cm$^3$ of dry $CH_3CN$ which were placed in a glass flask 0.170 g (0.39 mmol) of $C_4F_9SO_2N(CF_3)_2$ were added. The reaction mixture was stirred at room temperature till all RbF was dissolved (some minutes). The resulting mixture was examined by $^{19}F$ NMR spectroscopy. The signal at −37.8 ppm(s) belongs to the Rb$^+$ $^-N(CF_3)_2$ salt.

EXAMPLE 3

Preparation of Bis(trifluoromethyl)imido-rubidium Salt from $(CF_3)NSO_2N(CF_3)_2$ To 0.064 g (0.61 mmol) of RbF in 1.5 cm$^3$ of dry $CH_3CN$ which are placed in a glass flask 0.120 g (0.32 mmol) of $C_4F_9SO_2N(CF_3)_2$ were added. The reaction mixture was stirred at room temperature till all RbF was dissolved. The resulting mixture was examined by $^{19}F$NMR spectroscopy. The signal at −37.2 ppm(s) belongs to the Rb$^+$ $^-N(CF_3)_2$ salt.

The same procedure can be used for the preparation of bis(trifluoromethyl)imido-sodium, -potassium and -caesium salts.

EXAMPLE 4

Preparation of Bis(trifluoromethyl)imido-rubidium Salt from $C_3F_7CON(CF_3)_2$

To 0.092 g (0.88 mmol) of RbF suspended in 1.5 cm$^3$ of dry $CH_3CN$ in a glass flask 0.160 g (0.45 mmol) of $C_3F_7CON(CF_3)_2$ was added. The reaction mixture was stirred at room temperature till all RbF was dissolved (approximately 10 min.). The resulting mixture was examined by $^{19}F$ NMR spectroscopy. The signal at −37.2 ppm(s) belongs to the Rb$^+$ $^-N(CF_3)_2$ salt and the signals at −29.0 ppm, −80.8 ppm, −122.3 ppm and −125.9 ppm reflect the presence of $CF_3CF_2CF_2CF_2O^-$ anion in the reaction mixture.

After addition of $BrCH_2COOC_2H_5$ to the reaction mixture and heating at 80° C. during one hour the formation of substituted product, $(CF_3)_2NCH_2$—$COOC_2H_5$ was fixed by $^{19}F$ NMR spectroscopy and GC analyses. By the dilution of the reaction mixture with water $(CF_3)_2NCH_2COOC_2H_5$ was isolated as a pure substance (for details see example 8).

EXAMPLE 5

Preparation of Bis(trifluoromethyl)imido-silver Salt from $CF_3SO_2N(CF_3)_2$

To 0.080 g (0.63 mmol) of AgF in 1 cm$^3$ of dry $CH_3CN$ which were placed in a glass flask equipped with a condenser 0.180 g (0.63 mmol) of $CF_3SO_2N(CF_3)_2$ were added. The reaction mixture was stirred at room temperature for two hours. The resulting mixture was examined by $^{19}F$ NMR spectroscopy. The signal at −47.0 ppm(s) belongs to the Ag$^+$ $^-N(CF_3)_2$ salt. After addition of $C_6H_5CH_2Br$ to the reaction mixture and heating at 80° C. for 10 minutes the formation of substituted product $C_6H_5CH_2N(CF_3)_2$, was fixed by $^{19}F$ NMR spectroscopy and GC analyses. By dilution of the reaction mixture with water $C_6H_5CH_2N(CF_3)_2$ was isolated as a pure substance (for details see example 9).

EXAMPLE 6

Preparation of Bis(trifluoromethyl)imido-mercury Salt from $CF_3SO_2N(CF_3)_2$

The mixture of 0.17 g (0.54 mmol) of $HgF_2$, 0.32 g (1.1 mmol) of $CF_3SO_2N(CF_3)_2$ and 2 cm$^3$ of dry $CH_3CN$ was heated for 10 hours at 85° C. in a PTFE FEP cylinder, which was placed inside of a stainless-steel autoclave. After cooling, the clear liquid was separated from the deposit and examined by $^{19}F$ NMR spectroscopy. The signal at −46.3 ppm(s) belongs to $Hg[N(CF_3)_2]_2$salt. Published value for $Hg[N(CF_3)_2]_2$ is −48.7 ppm (broad singlet) (R. C. Dobbie and H. J. Emeleus, J. Chem. Soc. (1996) (1), p. 367–370).

EXAMPLE 7

Preparation of Bis(trifluoromethyl)imido-copper Salt from $CF_3SO_2N(CF_3)_2$

The mixture of 0.11 g (1.1 mmol) of $CuF_2$, 0.98 g (3.4 mmol) of $CF_3SO_2N(CF_3)_2$ and 1.5 cm$^3$ of dry $CH_3CN$ was heated for 10 hours at 80° C. in a PTFE FEP cylinder, which was placed inside of a stainless-steel autoclave. After cooling, the clear liquid was separated from the deposit and heated up to 80° C. in an argon stream to remove all volatile products. The residue was examined by $^{19}F$ NMR spectroscopy. The signal at −55.8 ppm (broad singlet) belongs to the $Cu[N(CF_3)_2]_2$ salt. After addition of Rb$^+$ $^-N(CF_3)_2$ salt to this solution in $CH_3CN$ only one average signal at −38.0 ppm (broad singlet) which belongs to the $^-N(CF_3)_2$ anion was observed in the $^{19}F$ NMR spectra.

Application of bis(trifluorormethyl)imido salts for introduction of the $N(CF_3)_2$ group into organic compounds:

EXAMPLE 8

Reaction of Bis(trifluoromethyl)imido-rubidium Salt with Ethyl Bromoacetate To the solution of $Rb^+$ $^-N(CF_3)_2$ salt which was obtained from 2.185 g of RbF and 6.127 g of $CF_3SO_2N(CF_3)_2$ in dry acetonitrile (see example 1) 3.13 g (18.7 mmol) of $BrCH_2COOC_2H_5$ were added. The mixture was kept boiling during one hour and diluted with water. The water insoluble liquid material was collected, washed with water and dried with $MgSO_4$. After distillation 2.73 g of pure $(CF_3)_2NCH_2COOC_2H_5$ were obtained.

Yield: 61%, B.p. 127128 'C. [6]. $^{19}F$ NMR spectra: δ $(CF_3)=57.0$ ppm(s) [6]. $^1H$ NMR spectra: $δ(CH_2)=4.3$ ppm (s).

EXAMPLE 9

Reaction of Bis(trifluoromethyl)imido-rubidium Salt with Benzyl Bromide

To the solution of $Rb^+$ $^-N(CF_3)_2$ salt (see example 1) which was obtained from 0.882 g (8.44 mmol) of RbF and 2.5 g (8.77 mmol) of $CF_3SO_2N(CF_3)_2$ in 7 cm³ of dry acetonitrile 1.27 g (7.4 mmol) of $C_6H_5CH_2Br$ were added. The mixture was kept boiling during one hour and diluted with water. The water insoluble liquid material was extracted with diethylether (3×5 cm³), washed with water and dried with $MgSO_4$. After distillation 1.35 g of pure $C_6H_5CH_2N(CF_3)_2$ were obtained.

Yield 75%, B.p. 151–152° C. $^{19}F$ NMR spectra: δ $(CF_3)=$ 56.8 ppm(t), $J_{H,F}=1.5$ Hz. $^1H$ NMR spectra: δ $(CH_2)=4.5$ ppm (q).

Reaction of $Rb^+$ $^-N(CF_3)_2$ salt with benzyl chloride was done in the same way as described above, except that the reaction mixture was kept boiling for 10 hours.

What is claimed:

1. A process for the generation of $N(CF_3)_2$ anions comprising reacting a sulphonamide of formula $$R_FSO_2N(CF_3)_2$$

wherein
  $R_F=F$ or $C_nF_{2n+1}$, and
  n=1–4,
with a metal fluoride of formula $$MF_x$$

wherein
  M=Na, K, Rb, Cs, Ag, Cu or Hg, and
  x=1 or 2, with the proviso that x=1, if M is Na, K, Rb, Cs or Ag, and that x=2, if M is Cu or Hg,
forming an imino salt of formula $$M^{x+}[N(CF_3)_2]_x$$

and the corresponding sulphonylfluoride of formula $$R_FSO_2F$$

or
reacting a sulphondiamide of formula $$(CF_3)_2N(SO_2CF_2)_mSO_2N(CF_3)_2$$

wherein
  m=0 or 1,
with a metal fluoride of formula $$MF_x$$

forming an imino salt $$M^{x+}[N(CF_3)_2]_x$$

and the corresponding sulphonyldifluoride of formula $$F(SO_2CF_2)_m SO_2F$$

or
reacting a N,N-Bis(trifluoromethyl)perfluoroacylamide of formula $$R_FCON(CF_3)_2$$

with a metal fluoride of formula $$MF_x$$

forming an imino salt $$M^{x+}[N(CF_3)_2]_x$$

and a salt of the formula $$R_FCF_2O^-M^+.$$

2. A process according to claim 1, wherein the reaction takes place in an organic solvent.

3. A process according to claim 1, wherein the reaction takes place in acetonitrile.

4. A process according to claim 1, wherein the reaction takes place in an organic solvent, which is free of water.

5. A process according to claim 1, wherein the reaction proceeds at a temperature of 15–100° C.

6. A process according to claim 1, wherein the reaction proceeds at room temperature.

7. A process according to claim 1, wherein the metal fluoride is rubidium fluoride.

8. A process according to claim 1, further comprising collecting and transforming the sulfonylfluoride into $$R_FSO_2N(CF_3)_2,$$

$$(CF_3)_2N(SO_2CF_2)_mSO_2N(CF_3)_2$$

or $$R_FCON(CF_3)_2.$$

9. A process according to claim 2, wherein the organic solvent is acetonitrile, ethylenglycoldimethylether, DMF or a mixture thereof.

10. A process according to claim 8, further comprising recycling the $$R_FSO_2N(CF_3)_2,$$

$$(CF_3)_2N(SO_2CF_2)_mSO_2N(CF_3)_2$$

or $$R_FCON(CF_3)_2$$

into the process.

11. A method of substituting a halogen or other group in an organic molecule comprising using as a reagent an imino salt of the formula $Ag^+[N(CF_3)_2]$.

12. A method of substituting a halogen or other group in an organic molecule comprising using as a reagent an imino salt of the formula $Cu^{2+}[N(CF_3)_2]_2$.

13. A method of substituting a halogen or other group in an organic molecule comprising using as a reagent an imino salt of the formula $$M^{x+}[N(CF_3)_2]_x$$

wherein

M=Na, Rb, Ag, Cu or Hg, and x=1 or 2, with the proviso that x=1, if M is Na, Rb, or Ag, and that x=2, if M is Cu or Hg, wherein the imino salt is prepared by a method according to claim 1.

14. A method of substituting a halogen or other group in an organic molecule comprising using as a reagent an imino salt of the formula $$M^{x+}[N(CF_3)_2]_x$$

wherein

M=Na, K, Cs, Rb, Ag, Cu or Hg, and x=1 or 2, with the proviso that x=1, if M is Na, Rb, K, CS or Ag, and that x=2, if M is Cu or Hg, wherein the imino salt is prepared by a method according to claim 1.

15. A method according to claim 11, wherein the group substituted in the organic molecule is a halogen.

16. A method according to claim 12, wherein the group substituted in the organic molecule is a halogen.

17. A method according to claim 13, wherein the group substituted in the organic molecule is a halogen.

18. A method according to claim 14, wherein the group substituted in the organic molecule is a halogen.

* * * * *